United States Patent [19]

Merkus

[11] Patent Number: 5,942,251

[45] Date of Patent: Aug. 24, 1999

[54] PHARMACEUTICAL COMPOSITIONS FOR INTRANASAL ADMINISTRATION OF DIHYDROERGOTAMINE

[76] Inventor: Franciscus W. H. M. Merkus, Grootreesdijk 26, Kasterlee, Belgium

[21] Appl. No.: 09/062,633

[22] Filed: Apr. 17, 1998

Related U.S. Application Data

[62] Division of application No. 08/525,771, filed as application No. PCT/EP94/00891, Mar. 18, 1994, Pat. No. 5,756,483.

[30]  Foreign Application Priority Data

| Mar. 26, 1993 | [BE] | Belgium | 9300297 |
| Mar. 26, 1993 | [BE] | Belgium | 9300298 |
| Mar. 26, 1993 | [BE] | Belgium | 9300299 |

[51] Int. Cl.⁶ .................................................. A61K 9/14
[52] U.S. Cl. .......................................... 424/493; 514/249
[58] Field of Search ........................... 424/493; 514/247

[56] References Cited

U.S. PATENT DOCUMENTS

| 4,659,696 | 4/1987 | Hirai et al. ........................ 514/15 |
| 4,727,064 | 2/1988 | Pitha . | |
| 4,834,985 | 5/1989 | Elger et al. ....................... 424/488 |
| 5,169,840 | 12/1992 | Kiechel et al. . | |
| 5,506,203 | 4/1996 | Buckstran et al. .................. 514/4 |
| 5,602,112 | 2/1997 | Rubinfeld . | |
| 5,624,898 | 4/1997 | Frey ........................................ 514/12 |
| 5,629,011 | 5/1997 | Illum ...................................... 424/434 |

FOREIGN PATENT DOCUMENTS

| 0094157 | 11/1983 | European Pat. Off. . |
| 0205282 | 12/1986 | European Pat. Off. . |
| 0463653 | 1/1992 | European Pat. Off. . |
| 0475482 | 3/1992 | European Pat. Off. . |
| 4207922 | 9/1993 | Germany . |
| 1592563 | 7/1981 | United Kingdom . |
| WO9109599 | 7/1991 | WIPO . |
| WO9315737 | 8/1993 | WIPO . |

OTHER PUBLICATIONS

Deutsche Apotheker Zeitung, vol. 130, No. 44, Nov. 1, 1990, pp. 2411–2415, Hermens and Merkus, Entitled "Nasale Arneimittel".

Humbert et al., Clin. Pharmacol Ther. 1996; 60:265–275, *Human Pharmacokinetics of Dihydroergotamine Administered by Nasal Spray*.

Abstract, in press *British Journal of Clinical Pharmacology*, 1998, *Pharmacokinetics of Intranasal Formulations of Dihydroergotamine*.

Marttin et al., Journal of Pharmaceutical Sciences, vol. 86, No. 7, Jul. 1997, *Nasal Absorption of Dihydroergotamine from Liquid and Powder Formulations*.

Martindale, *The Extra Pharmacopoeia*, 1996, p. 480.

*Primary Examiner*—James H. Reamer
*Attorney, Agent, or Firm*—Jones, Day, Reavis & Pogue

[57]  ABSTRACT

The invention relates to pharmaceutical compositions for the intranasal administration of dihydroergotamine, apomorphine and morphine comprising one these pharmacologically active ingredients in combination with a cyclodextrin and/or a disaccharide and/or a polysaccharide and/or a sugar alcohol.

36 Claims, No Drawings

PHARMACEUTICAL COMPOSITIONS FOR INTRANASAL ADMINISTRATION OF DIHYDROERGOTAMINE

This application is a Division of Ser. No. 08/525,771, filed Dec. 4, 1995, now U.S. Pat. No. 5,756,483, which is a 371 of PCT/EP94/00891 filed Mar. 18, 1994.

This invention is related to pharmaceutical compositions for nasal administration of dihydroergotamine, apomorphine and morphine, and methods of administering such compositions.

Dihydroergotamine mesylate (DHE) has been used in migraine therapy already for a long time. In patients with migraine attacks, DHE is suitable for basic interval treatment using tablets or solution, both for oral application, as well as for acute treatment by intravenous or intramuscular injection. DHE has been introduced in a nasal spray to avoid the parenteral and the oral route of administration. The nasal spray seems a good alternative, because it is less painful, less expensive and less inconvenient than injection therapy. Secondly, nausea and vomiting are common in migraine patients, making a nasal spray much more efficient than oral treatment.

A nasal spray containing DHE 4 mg/ml in an aqueous solution has been studied extensively by a number of investigators. Some of these investigators report, that besides DHE the nasal spray also contains glucose 5% and caffeine 1%. It was found that 1 mg of DHE, nasally administered, had the equivalence of 10 mg orally, and almost 40% of the bioavailability of the i.m. administration (P G Andersson and L T Jespersen, Cephalalgia 1986; 6: 51–54).

The maximal venoconstrictor effect of 1 mg nasal DHE amounted to about 40%, of 0.5 mg i.m. DHE to about 50% of the initial venous diameter (W. H. Aellig and J. Rosenthaler, Eur. J. Clin. Pharmacol. 1986; 30: 581–584).

Nasal DHE appeared to be equally effective than a combination of oral ergotamine and caffeine in relieving migraine attacks (D. Hirt et al, Cephalalgia 1989; 9, suppl. 10: 410–411). Another study in 904 patients confirmed the efficacy of nasal DHE and reported side effects in 18.4% of patients: nasal irritation, nausea, vomiting, fatigue, vertigo, breathlessness, tachycardia and perspiration. Only 3.9% of the patients refused further treatment with nasal DHE (G. Jenzer and M. F. Bremgartner, Schweiz. Rundsch. Med. Prax. 1990: 79: 914–917). Lataste et al (Cephalalgia 1989; 9 suppl. 10: 342–343) and Di Serio et al (Cephalalgia 1989; 9 suppl. 10: 344–345), confirm the efficacy of nasal DHE in the acute management of migraine. In contrast, Tulunay et al (Cephalalgia 1987; 7: 131–133) found little difference in nasal DHE and placebo.

Most of these studies are very encouraging and therefore nasal DHE, in the pharmaceutical composition studied by the above mentioned authors, seems an interesting alternative for oral and parenteral DHE preparations. Nasal DHE in the composition of DHE mesylate 4 mg/ml in 5% glucose and 1% caffeine, is available on prescription in several countries (e.g. Switzerland, France, Belgium).

Nevertheless, there is an urgent need for another DHE nasal drug formulation, because the nasal preparation, presently on the market, is not stable. It is on the market as a separate glass ampoule (containing the DHE formulation) which has to be broken by the patient and sprayed in the nose using a separate spray device. After opening of the ampoule, the spray can be used no longer than 24 hours.

Accordingly, it is an object of the invention to provide a highly stable pharmaceutical composition, suitable for nasal administration, capable of introducing efficiently a therapeutical amount of DHE into the human body. It has surprisingly been found that a pharmaceutically acceptable DHE composition can be formulated, suitable for nasal administration, without the presence of a special caffeine-glucose vehicle and without the necessity of presenting the formulation in a separate glass ampoule.

According to the invention, the nasal pharmaceutical composition contains DHE and/or a salt of DHE (mesylate or tartrate) and a cyclodextrin and/or other saccharides and/or sugar alcohols. Such compositions appear to result in a surprisingly high bioavailability and a superior stability of DHE.

The term "cyclodextrins" refers to cyclic oligosaccharides, like $\alpha$-, $\beta$- and $\gamma$-cyclodextrin and their derivatives, preferably $\beta$-cyclodextrin and its derivatives, preferably methylated $\beta$-cyclodextrin, with a degree of $CH_3$-substitution between 0.5 and 3.0, more preferably between 1.7 and 2.1. The term "saccharides" refers to disaccharides, like lactose, maltose, saccharose and also refers to polysaccharides, like dextrans, with an average molecular weight between 10.000 and 100.000, preferably 40.000 and 70.000. The term "sugar alcohols" refers to mannitol and sorbitol.

The nasal composition, according to the invention, can be administered as a nasal spray, nasal drop, suspension, gel, ointment, cream or powder. The administration of the nasal composition may also take place using a nasal tampon or nasal sponge, containing the invention composition.

In particular, powder formulations show a surprisingly high bioavailability and superior stability of the DHE. In addition, powder formulations have the advantage that no preservatives are necessary. Preservatives are known to decrease the ciliary movement, which may be harmful in chronic nasal medication (Hermens W. A. J. J. and Merkus F. W. H. M., Pharm. Res. 1987; 4: 445–449).

Nasal powder compositions can be made by mixing the active agent and the excipient, both possessing the desired particle size. Other methods to make a suitable powder formulation can be selected. Firstly, a solution of the active agent and the cyclodextrin and/or the other saccharide and/or sugar alcohol is made, followed by precipitation, filtration and pulverization. It is also possible to remove the solvent by freeze drying, followed by pulverization of the powder in the desired particle size by using conventional techniques, known from the pharmaceutical literature. The final step is size classification for instance by sieving, to get particles that are less than 100 microns in diameter, preferably between 50 and 100 microns in diameter. Powders can be administered using a nasal insufflator. Powders may also be administered in such a manner that they are placed in a capsule. The capsule is set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

Also the active agent can be brought into a viscous basis, using vehicles, conventionally used, for example natural gums, methylcellulose and derivatives, acrylic polymers (carbopol) and vinyl polymers (polyvinylpyrrolidone). In the invention compositions many other excipients, known from the pharmaceutical literature, can be added, such as preservatives, surfactants, co-solvents, adhesives, anti-oxidants, buffers, viscosity enhancing agents, and agents to adjust the pH or the osmolarity.

The required amount for a nasal administration of a liquid or semi-solid nasal administration form is generally between 0.05 ml and 0.2 ml, preferably about 0.1 ml per nostril. The amount of a powder nasal formulation is generally between 1 and 15 mg, preferably about 5 to 10 mg per nostril. Doses of DHE in the nasal pharmaceutical composition of the invention, suitable in the treatment of migraine attacks, are preferably in the range from 0.25 to 0.5 mg per nostril.

The following examples illustrate the invention in more detail, but are not construed as limiting the invention:

EXAMPLE 1 (liquid)

| Dihydroergotamine mesylate | 250 mg |
|---|---|
| Methyl-β-cyclodextrin D.S. 1.8 | 2.5 g |
| Benzalkonium Chloride | 0.01% |
| Sodium EDTA | 0.05–0.1% |
| Sorbitol | 5% |
| Purified water to | 100 ml |
| 100 μl = 250 μg DHE mesylate | |

EXAMPLE 2 (gel)

| Dihydroergotamine mesylate | 0.5 g |
|---|---|
| Methyl-β-cyclodextrin D.S. 1.8 | 5 g |
| Benzalkonium Chloride | 0.01% |
| Sodium EDTA | 0.05–0.1% |
| Sorbitol | 5% |
| Hydroxypropylmethylcellulose | 1–2% |
| Purified water to | 100 ml |
| 100 μl gel = 500 μg DHE | |

EXAMPLE 3A (powder)

| Dihydroergotamine mesylate | 0.5 mg |
|---|---|
| Methyl-β-cyclodextrin | 5 mg |
| Mannitol | 4.5 mg |
| 10 mg powder = 500 μg DHE mesylate | |

EXAMPLE 3B (powder)

| Dihydroergotamine mesylate | 0.5 mg |
|---|---|
| Dextran (average M.W. 70.000) | 9.5 mg |
| 10 mg powder = 500 μg DHE mesylate | |

EXAMPLE 3C (powder)

| Dihydroergotamine mesylate | 0.5 mg |
|---|---|
| β-cyclodextrin | 5 mg |
| Lactose | 4.5 mg |
| 10 mg powder = 500 μg DHE mesylate | |

Apomorphine is a very potent dopamine agonist. It is used as an adjunctive medication in the treatment of Parkinson's disease, complicated by motor fluctuations. Recently, encouraging results have been reported on the intranasal application of apomorphine in patients with Parkinson's disease to relieve "off-period" symptoms in patients with response fluctuations (T. van Laar et al, Arch. Neurol. 1992; 49: 482–484). The intranasal applied apomorphine, used by these authors, consisted of an aqueous solution of apomorphine HCl 10 mg/ml. This formulation is also used for parenteral application and is published in different Pharmacopoeia's.

The exact nasal composition formulation used in the study by T. van Laar et al (1992) was:

| Apomorphine HCl 0.5 H2O | 1 g |
|---|---|
| Sodium metabisulphite | 0.100 g |
| Sodium EDTA | 0.010 g |
| NaCl | 0.600 g |
| Benzalkonium Chloride | 0.01% |
| $NaH_2PO_4.2H_2O$ | 0.150 g |
| $Na_2HPO_4.2H_2O$ | 0.050 g |
| NaOH 1 M to adjust pH at 5.8 | |
| purified water to 100 ml | |
| (from Pharm. Weekblad 1991; 126: 1113–1114) | |

By a metered dose nebulizer a dose of 1 mg apomorphine HCl (0.1 ml of the solution) was delivered with each nasal application by puff to the patients. A great disadvantage of this aqueous solution is the instability of the apomorphine.

EP A 475 482 discloses stable dry pharmaceutical compositions containing a drug, such as for instance apomorphine, an excipient selected from a group of compounds including also lactose, and a water soluble alkaline stabilizer. This dry composition is very stable especially after a granulation process at high temperature. The process for preparing the dry composition is more rugged with the added water soluble alkaline stabilizer. The compositions described in EP A 475 482 are not appropriate and of no significance for nasal apomorphine administration.

EP 0 094 157 discloses a composition of drugs such as polypeptides, polysaccharides, aminoglycosides, β-lactam antibiotics and nucleic acids in combination with a cyclodextrin, preferably α-cyclodextrin, for nasal, vaginal or rectal administration. The drug apomorphine does not belong to any of the drug groups mentioned by EP 0 094 157.

EP A 463 653 discloses intranasal pharmaceutical compositions, in which cyclodextrins are added to a nasal drug formulation to reduce the undesirable side effect of the absorption enhancer in the formulation such as chelating agents, fatty acids, bile acids salts, surfactants, fusidic acid, lysophosphatides and cyclic peptide antibiotics. The main purpose is to protect the nasal mucosa from the undesirable effects of these absorption enhancers by adding a cyclodextrin to the formulation (col. 8, line 40–42). EP A 463 653 demonstrates in the examples that some cyclodextrins reduce the toxic effects of absorption enhancers including Laureth-9, Deoxycholic acid Sodium and L-α-lysophosphatidylcholine Palmitoyl. For the preparation of a nasal apomorphine composition according to the present invention, no such absorption enhancers are present or needed.

An object of the invention is a nasal formulation of apomorphine with an improved bioavailability and stability of apomorphine.

According to the invention, the nasal pharmaceutical composition contains apomorphine and/or apomorchine salts and a cyclodextrin and/or other saccharides and/or sugar alcohols. Such compositions appear to result in a surprisingly high bioavailability and superior stability of apomorphine.

The term "cyclodextrins" refers to cyclic oligosaccharides, like α-, β- and γ-cyclodextrin and their derivatives, preferably β-cyclodextrin and its derivatives, preferably methylated β-cyclodextrin, with a degree of $CH_3$-substitution between 0.5 and 3.0, more preferably between 1.7 and 2.1.

The term "saccharides" refers to disaccharides, like lactose, maltose, saccharose and also refers to polysaccharides, like dextrans, with an average molecular weight between 10.000 and 100.000, preferably 40.000 and 70.000. The term "sugar alcohols" refers to mannitol and sorbitol.

The nasal composition, according to the invention, can be administered as a nasal spray, nasal drop, suspension, gel, ointment, cream or powder. The administration of the nasal composition may also take place using a nasal tampon or nasal sponge, containing the invention composition.

In particular, powder formulations show a surprisingly high bioavailability and superior stability of the apomorphine.

In addition, powder formulations have the advantage that no preservatives are necessary. Preservatives are known to decrease the ciliary movement, which may be harmful in chronic nasal medication (Hermens W. A. J. J. and Merkus F. W. H. M., Pharm. Res. 1987; 4: 445–449).

Nasal powder compositions can be made by mixing the active agent and the excipient, both possessing the desired particle size. Other methods to make a suitable powder formulation can be selected. Firstly, a solution of the active agent and the cyclodextrin and/or the other saccharide and/or sugar alcohol is made, followed by precipitation, filtration and pulverization. It is also possible to remove the solvent by freeze drying, followed by pulverization of the powder in the desired particle size by using conventional techniques, known from the pharmaceutical literature. The final step is size classification for instance by sieving, to get particles that are less than 100 microns in diameter, preferably between 50 and 100 microns in diameter. Powders can be administered using a nasal insufflator. Powders may also be administered in such a manner that they are placed in a capsule. The capsule is set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

Also the active agent can be brought into a viscous basis, using vehicles, conventionally used, for example natural gums, methylcellulose and derivatives, acrylic polymers (carbopol) and vinyl polymers (polyvinylpyrrolidone). In the invention compositions many other excipients, known from the pharmaceutical literature, can be added, such as preservatives, surfactants, co-solvents, adhesives, anti-oxidants, buffers, viscosity enhancing agents, and agents to adjust the pH or the osmolarity.

The required amount for a nasal administration of a liquid or semi-solid nasal administration form is generally between 0.05 ml and 0.2 ml, preferably about 0.1 ml per nostril. The amount of a powder nasal formulation is generally between 1 and 15 mg, preferably about 5 to 10 mg per nostril. Doses of apomorphine in the pharmaceutical composition of the present invention, suitable in the treatment of Parkinson disease, are generally in the range of 0.1 to 2mg, preferably between 0.5 mg and 1 mg per nostril.

The following examples illustrate the present invention in more detail, but are not construed as limiting the invention:

EXAMPLE 1A (powder)

| | |
|---|---|
| Apomorphine base | 1 mg |
| Methyl-β-cyclodextrin D.S. 2.1 | 5 mg |
| Mannitol | 4 mg |
| 10 mg powder = 1 mg Apomorphine | |

EXAMPLE 1B (powder)

| | |
|---|---|
| Apomorphine HCl | 2 mg |
| Mannitol | 18 mg |
| 20 mg powder = 2 mg Apomorphine HCl | |

EXAMPLE 1C (powder)

| | |
|---|---|
| Apomorphine HCl | 1 mg |
| Dextran (average M.W. 70.000) | 9 mg |
| 10 mg powder = 1 mg Apomorphine HCl | |

EXAMPLE 2 (gel)

| | |
|---|---|
| Apomorphine HCl | 500 mg |
| Methylated-β-cyclodextrin D.S. 1.8 | 2.5 g |
| Hydroxypropylmethylcellulose | 1–2 g |
| Benzalkonium Chloride | 0.01% |
| Sodium EDTA | 0.1% |
| Sodium metabisulphite | 0.15% |
| Sorbitol | 4% |
| pH adjusted to | 4.5–5.5 |
| purified water to | 100 ml |
| 0.2 ml gel = 1 mg Apomorphine HCl | |

Morphine is one of the strongest analgesics. Morphine therapy is restricted to two groups of patients. Firstly, to hospitalized patients, after surgery and secondly, to cancer and burn patients. The latter treatment is chronic. Morphine is administered generally by injection and in chronic treatment by sustained release oral preparations. After single oral administration morphine has a poor effect, mainly due to a large first pass effect. Secondly, the oral route is not possible when the patient shows severe nausea, vomiting, bowel obstruction or confusion. There is a need for a non-parenteral administration, other than oral, because injection therapy needs interference of (para)medical personnel and is painful.

Buccal administration of morphine have been proposed (MDD Bell et al, Lancet 1985; 1: 71–73), but this route did not find a large acceptance in practice. Recently rectal administration of morphine has been studied (T. J. Wilkinson et al, Cancer Chemother. Pharmacol 1992; 31: 251–254 and N Babul et al Clin. Pharmacol. Ther. 1993; 54: 286–292). From both publications it can be concluded that rectal application in some cases may be an alternative when the parenteral route is impractical or undesirable and the oral route is not available due to the patients condition. Nasal administration of a strong analgesic could be a good alternative to parenteral therapy, because it may give a very rapid absorption and no first pass effect.

To overcome the drawbacks of the oral and parenteral routes of administration of morphine, the use of a nasal spray has been proposed (S. L. Verweij and R. van Gijn: Can morphine be administered nasally? Ziekenhuisfarmacie (Dutch) 1988; 4: 73–77). The composition of the nasal spray in this study was:

| | |
|---|---|
| Morphine HCl.3H₂O | 1.50 g |
| Sodium metabisulphite | 0.03 g |
| Sodium EDTA | 0.003 g |
| Benzylalcohol | 0.3 ml |
| Propylene glycol | 6 ml |
| Phosphate Buffer (0.01 mol/L; pH 6.00) | 30 ml |
| Per puff of 100 μl the dose of morphine is | 5 mg. |

In 7 volunteers Verweij and van Gijn studied the pharmacokinetics of morphine after 4 puffs of about 100 μl (2 times 1 puff of 100, μl in each nostril). The exact dose which was delivered to the volunteers was 16 mg of morphine (range 15–18 mg) and the bioavailability of morphine from this nasal spray was 26–35%. The bioavailabilty of morphine after oral application is estimated to be about 40% (J. Säwe, Clin. Pharmacokinetics 1986; 11: 87–106). This means, that the bioavailability of morphine after giving the nasal spray as described by Verweij and van Gijn is relatively low. After nasal absorption there is no first pass effect and therefore the nasal bioavailability should be higher than the oral.

The nasal absorption of morphine has been studied also by F Chast et al (J. Pharm. Clin. 1992; 11: 257–261). They delivered nasally and orally 20 mg morphine acetate in an aqueous solution to 6 patients and compared the nasal absorption with the oral absorption of the same solution. They found, as expected, higher blood levels of morphine after the nasal application. Unfortunately, the nasal solutions, as described by the preceding studies of Verweij and van Gijn and of Chast and coworkers, are not stable and the bioavailability of morphine can be improved.

An object of the invention is to provide a highly stable pharmaceutical composition, suitable for nasal administration, and showing an superior bioavailability of morphine.

According to the invention, the nasal pharmaceutical composition contains morphine and/or morphine salts (hydrochloride, sulphate, acetate) and a cyclodextrin and/or other saccharides and/or sugar alcohols. Such compositions appear to result in a surprisingly high bioavailability and superior stability of morphine.

The term "cyclodextrins" refers to cyclic oligosaccharides, like α, β- and γ-cyclodextrin and their derivatives, preferably β-cyclodextrin and its derivatives, preferably methylated β-cyclodextrin, with a degree of CH₃-substitution between 0.5 and 3.0, more preferably between 1.7 and 2.1. The term "saccharides" refers to disaccharides, like lactose, maltose, saccharose and also refers to polysaccharides, like dextrans, with an average molecular weight between 10.000 and 100.000, preferably 40.000 and 70.000. The term "sugar alcohols" refers to mannitol and sorbitol.

The nasal composition, according to the invention, can be administered as a nasal spray, nasal drop, suspension, gel, ointment, cream or powder. The administration of the nasal composition may also take place using a nasal tampon or nasal sponge, containing the invention composition.

In particular, powder formulations show a surprisingly high bioavailability and superior stability of the morphine. In addition, powder formulations have the advantage that no preservatives are necessary. Preservatives are known to decrease the ciliary movement, which may be harmful in chronic nasal medication (Hermens W. A. J. J. and Merkus F. W. H. M., Pharm. Res. 1987; 4: 445–449).

Nasal powder compositions can be made by mixing the active agent and the excipient, both possessing the desired particle size. Other methods to make a suitable powder formulation can be selected. Firstly, a solution of the active agent and the cyclodextrin and/or the other saccharide and/or sugar alcohol is made, followed by precipitation, filtration and pulverization. It is also possible to remove the solvent by freeze drying, followed by pulverization of the powder in the desired particle size by using conventional techniques, known from the pharmaceutical literature. The final step is size classification for instance by sieving, to get particles that are less than 100 microns in diameter, preferably between 50 and 100 microns in diameter. Powders can be administered using a nasal insufflator. Powders may also be administered in such a manner that they are placed in a capsule. The capsule is set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

Also the active agent can be brought into a viscous basis, using vehicles, conventionally used, for example natural gums, methylcellulose and derivatives, acrylic polymers (carbopol) and vinyl polymers (polyvinylpyrrolidone). In the invention compositions many other excipients, known from the pharmaceutical literature, can be added, such as preservatives, surfactants, co-solvents, adhesives, anti-oxidants, buffers, viscosity enhancing agents, and agents to adjust the pH or the osmolarity.

The required amount for a nasal administration of a liquid or semi-solid nasal administration form is generally between 0.05 ml and 0.2 ml, preferably about 0.1 ml per nostril. The amount of a powder nasal formulation is generally between 1 and 15 mg, preferably about 5 to 10 mg per nostril.

Doses of morphine in the pharmaceutical composition of the present invention, suitable in the treatment of pain, are in the range from 1 to 20 mg.

The following examples illustrate the present invention in more detail, but are not construed as limiting the invention:

EXAMPLE 1A (powder)

| | |
|---|---|
| Morphine sulphate 5H₂O | 13.3 mg |
| Methyl-β-cyclodextrin D.S. 2.1 | 11.7 mg |
| Mannitol | 5 mg |
| 30 mg powder = 10 mg morphine | |

EXAMPLE 1B (powder)

| | |
|---|---|
| Morphine sulphate 5H₂O | 13.3 mg |
| β-cyclodextrin | 6.7 mg |
| 20 mg powder = 10 mg morphine | |

EXAMPLE 1C (powder)

| | |
|---|---|
| Morphine HCl 3H₂O | 13.1 mg |
| Dextran (average MW 70.000) | 16.9 mg |
| 30 mg powder = 10 mg morphine | |

EXAMPLE 2 (gel)

| | |
|---|---|
| Morphine (as salt) | 1.5 g |
| Methyl-β-cyclodextrin D.S. 1.8 | 5 g |
| (Hydroxypropyl)methylcellulose | 1–2% |
| Benzalkonium Chloride | 0.01% |
| Sodium EDTA | 0.1% |
| Sodium metabisulphite | 0.15% |
| Sorbitol | 4% |
| Purified water to | 50 ml |
| 0.2 ml gel = 6 mg morphine | |

EXAMPLE 3 (liquid)

| | |
|---|---|
| Morphine (as salt) | 4 g |
| Methyl-β-cyclodextrin D.S. 2.1 | 4 g |
| Methylcellulose | 0.25% |
| Sodium metabisulphite | 0.15% |
| Sodium EDTA | 0.1% |
| Benzalkonium Chloride | 0.01% |
| Mannitol | 4% |
| Purified water to | 100 ml |
| 100 μl = 4 mg morphine | |

I claim:

1. A pharmaceutical composition for nasal administration of a pharmacologically active ingredient to be absorbed through the nasal mucosa, wherein the pharmacologically active ingredient is selected from the group consisting of dihydroergotamine, dihydroergotamine salts and mixtures thereof, and the composition further comprises an ingredient selected from the group consisting of cyclodextrins, sugar alcohols, dextrans, and mixtures thereof, said pharmaceutical composition being essentially free of any toxic penetration or absorption promoter.

2. A pharmaceutical composition according to claim 1, wherein the dihydroergotamine salts are selected from the group consisting of dihydroergotamine mesylate, dihydroergotamine tartrate and mixtures thereof.

3. A pharmaceutical composition according to claim 1, wherein the cyclodextrins are selected from the group consisting of α-, β- and γ-cyclodextrins, derivatives of α-, β- and γ-cyclodextrins and mixtures thereof.

4. A pharmaceutical composition according to claim 1, wherein the cyclodextrins are selected from the group consisting of β-cyclodextrins, derivatives of β-cyclodextrins and mixtures thereof.

5. A pharmaceutical composition according to claim 4, wherein the derivatives of β-cyclodextrin comprise methylated β-cyclodextrins with a degree of substitution between about 0.5 and about 3.0.

6. A pharmaceutical composition according to claim 1, wherein the sugar alcohols are selected from the group consisting of mannitol, sorbitol and mixtures thereof.

7. A pharmaceutical composition according to claim 1 in powder form wherein the particles of the powder have a diameter between about 50 and about 100 microns.

8. A process for preparing a nasal pharmaceutical composition comprising combining a pharmaceutically active ingredient selected from the group consisting of dihydroergotamine, dihydroergotamine salts and mixtures thereof with an ingredient selected from the group consisting of cyclodextrins, dextrans, sugar alcohols and mixtures thereof.

9. A method of treating migraine attacks comprising administering to the nasal mucosa of a patient a pharmaceutical composition comprising a pharmacologically active ingredient selected from the group consisting of dihydroergotamine, dihydroergotamine salts and mixtures thereof in combination with an ingredient selected from the group consisting of cyclodextrins, dextrans, sugar alcohols and mixtures thereof.

10. A pharmaceutical composition according to claim 1, wherein said dextrans have average molecular weight between about 10,000 and about 100,000.

11. A pharmaceutical composition as claimed in claim 1, wherein said ingredient consists of one or more dextrans.

12. A pharmaceutical composition according to claim 1, wherein said ingredient is selected from the group consisting of cyclodextrins, dextrans and mixtures thereof.

13. A pharmaceutical composition according to claim 1, wherein said ingredient consists of one or more cyclodextrins.

14. A pharmaceutical composition for nasal administration consisting essentially of
    (a) a pharmacological active ingredient for absorption through the nasal mucosa and selected from the group consisting of dihydroergotamine, dihydroergotamine salts and mixtures thereof,
    (b) an ingredient selected from the group consisting of cyclodextrins, sugar alcohols, dextrans, and mixtures thereof,
    (c) optionally a pharmaceutically acceptable carrier,
    (d) optionally a preservative, and
    (e) optionally a viscosity control agent.

15. A pharmaceutical composition according to claim 14, wherein the dihydroergotamine salts are selected from the group consisting of dihydroergotamine mesylate, dihydroergotamine tartrate and mixtures thereof.

16. A pharmaceutical composition according to claim 14, wherein the cyclodextrins are selected from the group consisting of α-, β-, and γ-cyclodextrins, derivatives of α-, β-, and γ-cyclodextrins and mixtures thereof.

17. A pharmaceutical composition according to claim 14, wherein the cyclodextrins are selected from the group consisting of β-cyclodextrins, derivatives of β-cyclodextrins and mixtures thereof.

18. A pharmaceutical composition according to claim 17, wherein the derivatives of β-cyclodextrins comprise methylated β-cyclodextrins with a degree of substitution between about 0.5 and about 3.0.

19. A pharmaceutical composition according to claim 14, wherein the sugar alcohols are selected from the group consisting of mannitol, sorbitol and mixtures thereof.

20. A pharmaceutical composition according to claim 14 in powder form wherein the particles of the powder have a diameter between about 50 and about 100 microns.

21. A pharmaceutical composition according to claim 14, wherein said dextrans have average molecular weight between about 10,000 and about 100,000.

22. A pharmaceutical composition as claimed in claim 14, wherein said ingredient consists of one or more dextrans.

23. A pharmaceutical composition according to claim 14, wherein said ingredient is selected from the group consisting of cyclodextrins, dextrans and mixtures thereof.

24. A pharmaceutical composition according to claim 14, wherein said ingredient consists of one or more cyclodextrins.

25. A pharmaceutical composition for nasal administration, consisting essentially of
    (a) a pharmacological active ingredient for absorption through the nasal mucosa and selected from the group consisting of dihydroergotamine, dihydroergotamine salts and mixtures thereof, and (b) an ingredient selected from the group consisting of cyclodextrins, sugar alcohols, dextrans and mixtures thereof.

26. A pharmaceutical composition according to claim 25 in powder form.

27. A pharmaceutical composition according to claim 25, wherein the dihydroergotamine salts are selected from the group consisting of dihydroergotamine mesylate, dihydroergotamine tartrate and mixtures thereof.

28. A pharmaceutical composition according to claim 25, wherein the cyclodextrins are selected from the group consisting of α-, β- and γ-cyclodextrins, derivatives of α-, β- and γ-cyclodextrins and mixtures thereof.

29. A pharmaceutical composition according to claim 25, wherein the cyclodextrins are selected form the group consisting of β-cyclodextrins, derivatives of β-cyclodextrins and mixtures thereof.

30. A pharmaceutical composition according to claim 29, wherein the derivatives of β-cyclodextrin comprise methylated β-cyclodextrins with a degree of substitution between about 0.5 and about 3.0.

31. A pharmaceutical composition according to claim 25, wherein the sugar alcohols are selected from the group consisting of mannitol, sorbitol and mixtures thereof.

32. A pharmaceutical composition according to claim 26 wherein the particles of the powder have a diameter between about 50 and about 100 microns.

33. A pharmaceutical composition according to claim 25, wherein said dextrans have average molecular weight between about 10,000 and about 100,000.

34. A pharmaceutical composition as claimed in claim 25, wherein said ingredient consists of one or more dextrans.

35. A pharmaceutical composition according to claim 25, wherein said ingredient is selected from the group consisting of cyclodextrins, dextrans and mixtures thereof.

36. A pharmaceutical composition according to claim 25, wherein said ingredient consists of one or more cyclodextrins.

* * * * *